(12) United States Patent
Pedersen (10) Patent No.: US 8,827,648 B2
(45) Date of Patent: Sep. 9, 2014

(54) SERVICE CRANE FOR A WIND TURBINE (75) Inventor: Gunnar K. Storgaard Pedersen, Skjern (DK)

(73) Assignee: Vestas Wind Systems A/S, Aarhus N. (DK)

( * ) Notice: Subject to any disclaimer, the term of this patent is extended or adjusted under 35 U.S.C. 154(b) by 603 days.

(21) Appl. No.: 13/120,825

(22) PCT Filed: Sep. 30, 2009

(86) PCT No.: PCT/DK2009/050252
§ 371 (c)(1),
(2), (4) Date: Apr. 26, 2011

(87) PCT Pub. No.: WO2010/037392
PCT Pub. Date: Apr. 8, 2010

(65) Prior Publication Data
US 2011/0200435 A1 Aug. 18, 2011

Related U.S. Application Data (60) Provisional application No. 61/194,724, filed on Sep. 30, 2008.

(30) Foreign Application Priority Data

Sep. 30, 2008 (DK) .................. 2008 01364

(51) Int. Cl.
*F03D 11/00* (2006.01)
*F03D 1/00* (2006.01)
*C02F 5/08* (2006.01)
*C02F 5/02* (2006.01)
*C02F 1/461* (2006.01)

(52) U.S. Cl.
CPC ............ *F03D 1/003* (2013.01); *C02F 2209/06* (2013.01); *C02F 2201/46145* (2013.01); *C02F 2303/04* (2013.01); *C02F 2201/46115* (2013.01); *C02F 2201/4618* (2013.01); *Y02E 10/726* (2013.01); *C02F 2209/05* (2013.01); *C02F 5/083* (2013.01); *C02F 5/02* (2013.01); *C02F 2303/16* (2013.01); *C02F 2209/005* (2013.01); *A61L 2202/14* (2013.01); *C02F 2201/46125* (2013.01); *C02F 2201/46135* (2013.01); *C02F 2301/043* (2013.01); *C02F 1/4618* (2013.01)
USPC ................ 416/146 R; 416/204 R; 416/244 R (58) Field of Classification Search
USPC .......... 416/61, 62, 146 R, 204 R, 244 R, 248, 416/DIG. 6; 212/179; 29/889.1
See application file for complete search history.

(56) References Cited

U.S. PATENT DOCUMENTS 6,357,549 B1 * 3/2002 Brennan et al. ............... 182/133

FOREIGN PATENT DOCUMENTS

DE 202004016460 U1 * 12/2004
DE 10 2006 034 052 10/2007

(Continued)

OTHER PUBLICATIONS

Gleistein, Device for exchanging a rotor blade on a wind power machine, Dec. 23, 2004, Abstract of DE202004016460 U1.*

(Continued)

*Primary Examiner* — Ned Landrum
*Assistant Examiner* — Liam McDowell
(74) *Attorney, Agent, or Firm* — Wood, Herron & Evans, LLP (57) ABSTRACT

A service crane for a wind turbine having a nacelle and a hub. One or more wing blades is attached to the hub via a wing pitch bearing, and the service crane includes an attachment foundation for connection to the hub. The service crane is adapted to be mounted on the wind turbine during operation and to be dismounted when not being used. The attachment foundation of the service crane is mounted on the hub of the wind turbine via the wing pitch bearing.

11 Claims, 7 Drawing Sheets

(56) References Cited

FOREIGN PATENT DOCUMENTS

| | | |
|---|---|---|
| EP | 1 677 006 | 7/2006 |
| WO | 02/34664 | 5/2002 |
| WO | WO2007/135391 A2 * | 11/2007 |

OTHER PUBLICATIONS

Pavlos Avramidis; International Search Report and Written Opinion issued in priority International Application No. PCT/DK2009/050252; Jul. 21, 2010; 9 pages; European Patent Office.

European Patent Office, EP Communication issued in corresponding EP 09776297.5-2321 dated Dec. 21, 2012, 5 pages.

* cited by examiner

SERVICE CRANE FOR A WIND TURBINE

TECHNICAL FIELD OF THE INVENTION

The present invention relates to a service crane for a wind turbine comprising a nacelle and a hub. One or more wing blades is attached to the hub via a wing pitch bearing, and the service crane comprises an attachment foundation for connection to the hub. The service crane is adapted to be mounted on the wind turbine during operation and to be dismounted when not being used.

BACKGROUND ART

In the nacelle of a wind turbine, several heavy wind turbine components, such as gears, shafts, generators, etc., are arranged. From time to time, these components need maintenance, repair, or even replacement, and it is therefore often necessary to lower the components down from the nacelle and subsequently hoist them up again for installation in the nacelle.

In the prior art, several solutions are known for lowering wind turbine components down from the nacelle and hoisting them up. In one prior art solution, a typical crane at ground level is being used. However, since wind turbines are continually increasing in size, the components of the individual wind turbine are also increasing in sizes. Accordingly, typical cranes at ground level also need to be of a size where it is possible to handle the heavy components of the wind turbine. Thus, the costs for lowering and hoisting the components of the wind turbine by using ordinary ground-based cranes increase with the size of the wind turbine and the weight of the components which need to be handled. There is thus a need for a more cost-effective way of handling, i.e. lowering and hoisting, components from and to the nacelle.

In other solutions in the prior art, service cranes are permanently mounted either on the hub or the nacelle of the wind turbine. However, this increases the weight of the nacelle and thus the load on the tower of the wind turbine. In other solutions, the nacelle and the hub are arranged with crane foundations and attachment points, thus enabling service cranes to be lifted up and mounted on these foundations and attachment points when a service crane is necessary for the handling of the components from or to the nacelle. However, these foundations and attachments points must be provided with additional support and strengthening support so that the service crane may handle high loads, which also increase the weight of the nacelle and thereby the load placed on the tower of the wind turbine.

SUMMARY OF THE INVENTION

An object of the present invention is, at least partly, to overcome the above disadvantages and drawbacks of the prior art. More specifically, it is an object to provide a service crane which may easily be mounted on a wind turbine.

It is also an object of the present invention to provide a solution where separate crane foundations and attachment points on the nacelle are avoided.

The above objects, together with numerous other objects, advantages, and features which will become evident from the below description, are accomplished by a solution in accordance with the present invention, wherein the attachment foundation of the service crane is mounted on the hub of the wind turbine via the wing pitch bearing.

Hereby it is obtained that the service crane may be mounted on the wind turbine by using the already existing attachment devices on the hub and nacelle. Thus, separate foundations and attachment devices need not to be implemented on the wind turbine as in the prior art, whereby the nacelle and hub may have an overall lower weight. A further advantage of using the wing pitch bearing for attachment of the service crane is that the wing pitch bearing already is constructed for handling high loads.

In addition, the attachment foundation may mainly be connected to the wing pitch bearing from an outside of the hub so that mounting of the service crane on the hub is facilitated. Furthermore, by mounting the attachment foundation from the outside of the hub, it is also obtained that the main part of the service crane is placed outside the hub. In this way, it is operable in an area outside the hub, which is an advantage when the service crane is used to handle wind turbine components.

In an embodiment according to the invention, at least one wing blade may be dismounted from the wing pitch bearing before mounting the crane. Hereby it is obtained that the wing pitch bearing is uncovered, thus facilitating the attachment of the attachment foundation of the service crane to the wing pitch bearing. Furthermore, the service crane may have a larger operating area since it does not need to operate around the wing blade.

When dismounted, the wing blade may be attached to the tower of the wind turbine, thus facilitating the wing blade handling. Furthermore, the handling operation of lowering the wing blade to ground level is avoided.

In one embodiment, the attachment foundation may have a U-shaped, a horse shoe-shaped, or partly circular configuration. Hereby it is obtained that the attachment foundation has substantially the same configuration as the wing pitch bearing, so that the main part of the attachment foundation may be aligned with the wing pitch bearing.

The attachment foundation may be connected with the wing pitch bearing in the same manner as the wing blade is connected with the wing pitch bearing, thus facilitating the attachment and fastening of the service crane to the wind turbine.

Alternatively, the attachment foundation may be arranged around the wing blade. It is thus obtained that it will not be necessary to remove the wing blade from the hub. Instead, some of the fastening devices, which hold and fixate the wing blade in the hub, may be removed, and the attachment foundation may afterwards be placed around the wing blade using for instance the threaded holes of the wing pitch bearing for the fastening and fixation of the attachment foundation of the service craned to the wing pitch bearing.

In one embodiment according to the invention, the attachment foundation may comprise two arms and a pivot joint situated for a pivotable connection of the arms, enabling the arms of the attachment foundation to turn around the pivot joint, thereby facilitating that the attachment foundation can be placed around the wing blade.

In addition, the wing pitch bearing may comprise a fixed part and a turnable part, the turnable part being arranged either on an inside of the fixed part or on an outside of the fixed part. The attachment foundation may be connected with the fixed part and/or the turnable part.

The turnable part of the wing pitch bearing may be adapted to turn the service crane during operation. A further advantage of using the wing pitch bearing as attachment point for the service crane is that the wing pitch bearing may be used for turning and thereby operating the service crane.

The service crane may comprise a turning device for turning the service crane when the attachment foundation is connected to the fixed part of the wing pitch bearing.

In one embodiment, the wing pitch bearing and/or the hub may comprise locking means. Hereby it is obtained that the service crane may be fixated and held in a predetermined position so that it will not start turning unintendedly during operation.

In another embodiment, the attachment foundation may be connected with the wing pitch bearing via bolts. The wing blade is attached to the wing pitch bearing via fastening devices, such as bolts, and it is therefore an advantage to attach also the service crane to the wing pitch bearing with the same size bolts as are being used for the attachment of the wing blade.

The present invention also relates to a wind turbine comprising a service crane having the above-mentioned features.

Moreover, the present invention relates to a method for mounting a service crane on a wind turbine, the method comprising the steps of:

dismounting a wing blade from a wing pitch bearing of a hub, and mounting an attachment foundation of the service crane on the wing pitch bearing.

Furthermore, when dismounted, the wing blade may be lowered onto the ground or be attached to the tower of the wind turbine.

Additionally, a nacelle of the wind turbine may be yawed away from the wing blade when the wing blade has been attached to the tower, and before the attachment foundation is connected with the wing pitch bearing.

The present invention also relates to another method for mounting a service crane on a wind turbine, which method comprises the steps of:

removing one or more fastening devices from a wing pitch bearing of a hub, the fastening devices being adapted to hold a wing blade in place on the wing pitch bearing, arranging an attachment foundation around the wing blade, and mounting the attachment foundation on the wing pitch bearing by means of fastening devices.

BRIEF DESCRIPTION OF THE DRAWINGS

The invention and its many advantages will be described in more detail below with reference to the accompanying schematic drawings, which for the purpose of illustration show some non-limiting embodiments and in which.

All the drawings are strictly schematic and not necessarily to scale, and they show only those parts which are necessary in order to elucidate the invention, other parts being omitted or merely suggested.

DESCRIPTION OF PREFERRED EMBODIMENTS

Figure 1:
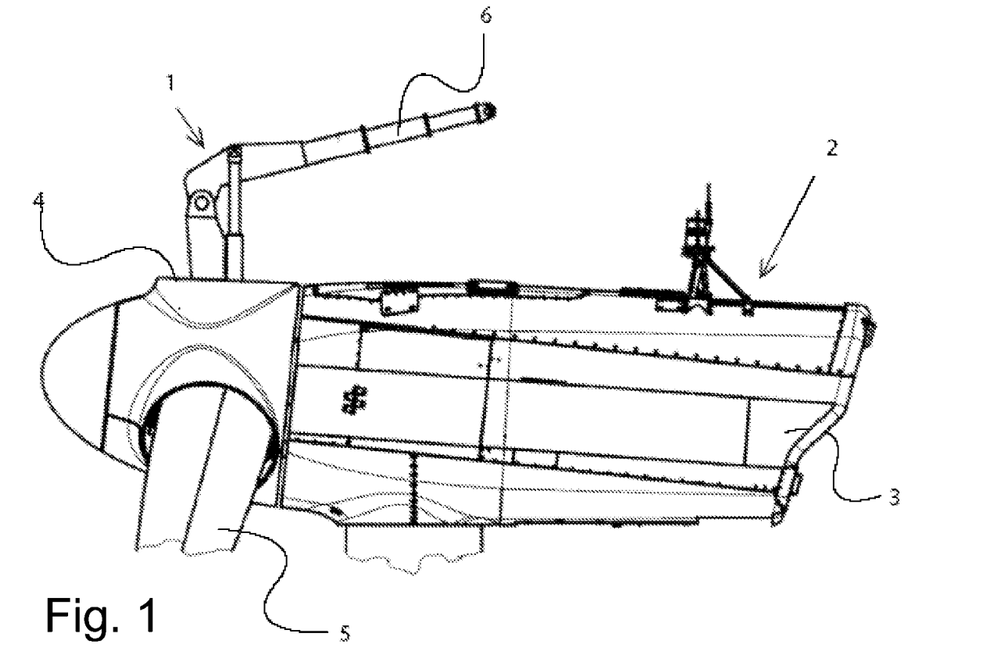
FIG. 1 shows a service crane according to the invention attached to the hub of a nacelle, said service crane being ready for use.

In FIG. 1, the service crane 1 according to the invention is shown mounted on a wind turbine 2. The wind turbine 2 comprises a nacelle 3 and a hub 4. One or more wing blades 5 are attached to the hub 4 via a wing pitch bearing (not shown).

In this embodiment, one of the wing blades 5 has been removed from the hub 4 and the attachment foundation (not shown) of the service crane 1 according to the invention has been connected with the wing pitch bearing instead. The service crane 1 is mainly connected to the wing pitch bearing from an outside of the hub 4 so that the main part of the service crane 1 is placed outside the hub 2 and thereby operable in an large area outside the hub 2. In this way, a flexible service crane 1 with a large operating area is provided.

In this embodiment, the service crane 1 comprises a telescope arm 6, which may be extended in relation to the intended operation area of the service crane 1. In other embodiments, the service crane 1 may have other designs.

Figure 2:
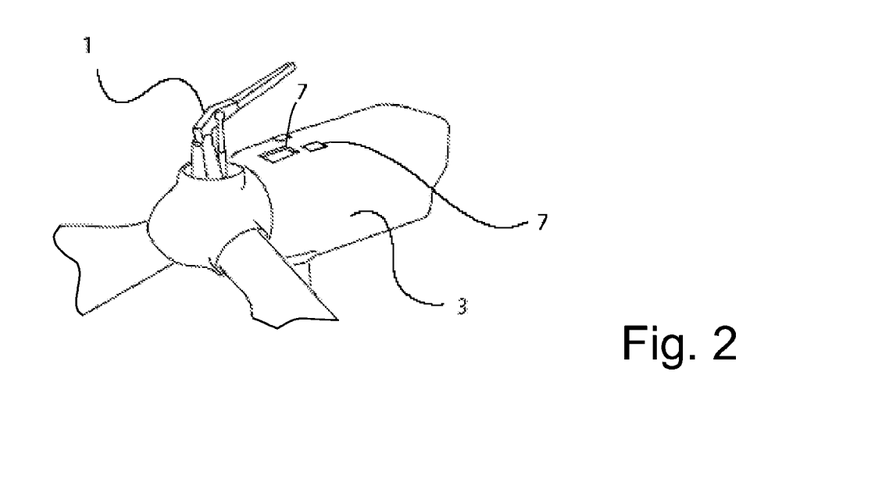
FIGS. 2-5 show different views of the service crane.
Figure 3:
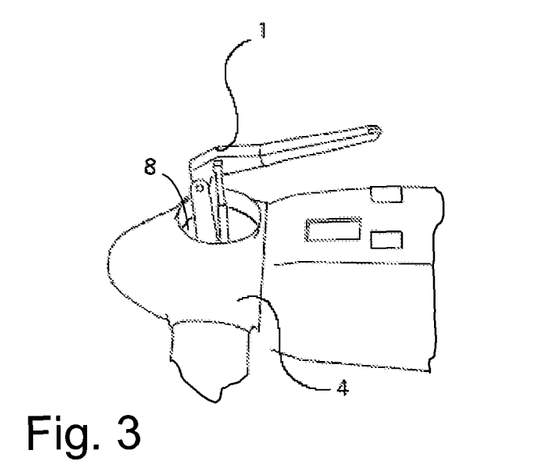
Figure 4:
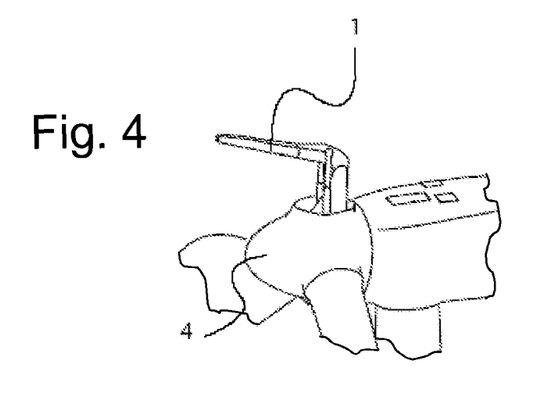
Figure 5:
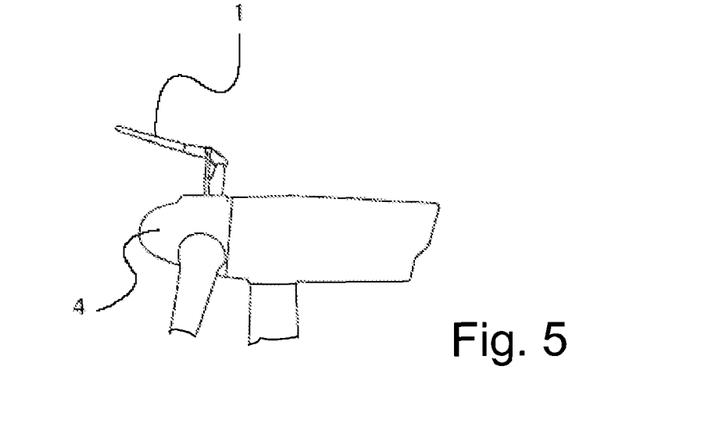

In FIGS. 2 to 5, the service crane 1 is shown from different perspectives. In FIG. 2, several hatches 7 are shown in the top of the nacelle 3, enabling the lifting device (not shown) of the service crane 1 to be lowered through the hatches, whereby components inside the nacelle 3 can be lifted out from the nacelle 3. In FIG. 3, the attachment foundation 8 of the service crane 1 is shown connected with the wing pitch bearing of the hub 4. FIGS. 4 and 5 show the service crane 1 turned so that the telescopic arm is extending out from the front part of the hub 4, whereby components may be lowered down to the ground as well as hoisted up to the nacelle 3. The telescopic arm of the service crane 1 may be extended in view of the size of the components being handled by the service crane 1. The service crane 1 may be turned in the same way as the wing blade is turned/pitched, i.e. by turning the wing pitch bearing.

Figure 6:
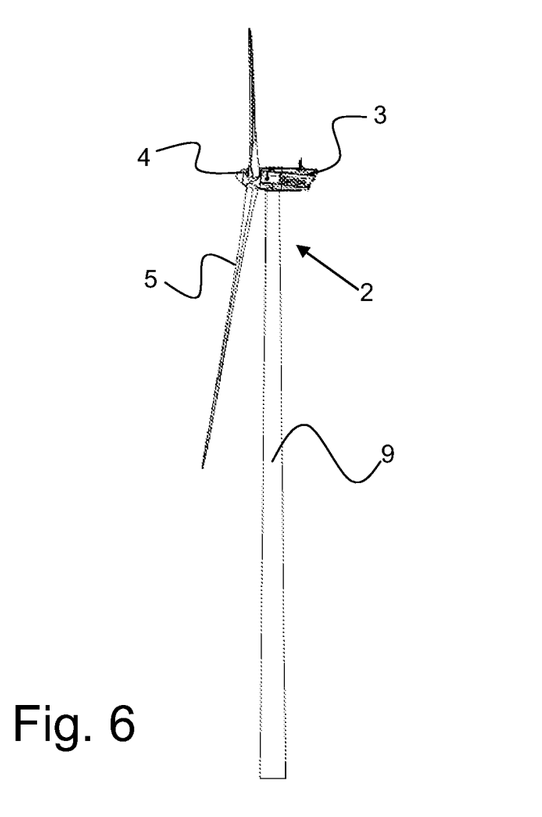
FIGS. 6-12 show one method according to the invention of mounting the service crane on a wind turbine.
Figure 7:
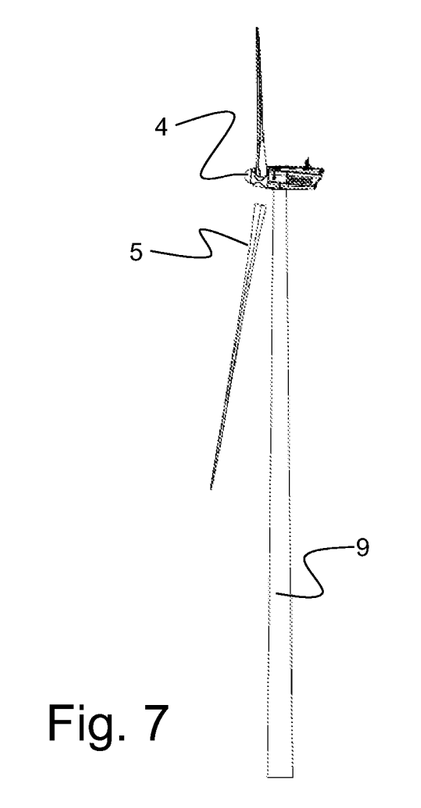

In FIGS. 6 to 12, a sequence of views of one embodiment of a method for mounting a service crane 1 on the wind turbine is shown. FIG. 6 shows a wind turbine 2 from the side, the wind turbine 2 comprising a nacelle 3, a hub 4, and a tower 9. Three wing blades 5 are attached to the hub 4. In FIG. 7, one of the wing blades 5 is detached from the hub 4 so that the wing pitch bearing (not shown) is uncovered by the wing blade 5. The wing blade 5 may either be placed on the tower 9 or lowered down to the ground.

When the wing blade 5 is attached to the tower 9, the nacelle 3 may preferably be yawed away from the place where the wing blade is attached, so that, when the service crane 1 is hoisted up to the hub, the wing blade on the tower will not interfere with this hoisting. A further advantage of yawing the nacelle 3 is that the wing blade 5 on the tower 9 will not interfere with the hoisting procedures of the components of the nacelle either.

Figure 8:
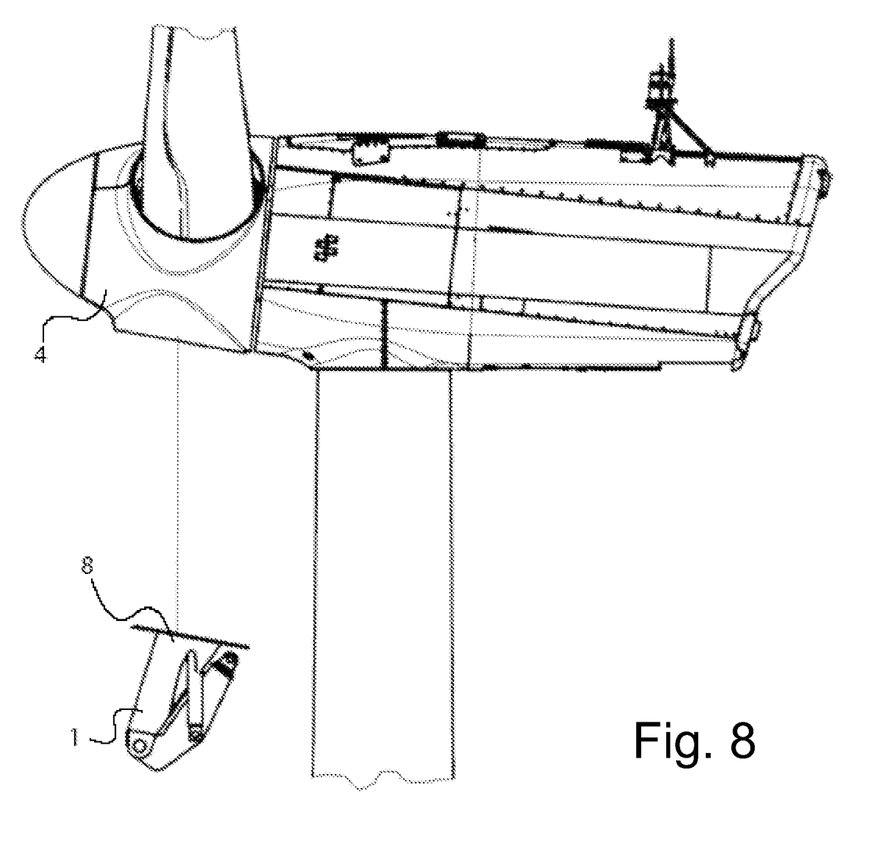

Subsequently, the service crane 1 is hoisted up to the hub 4, which is shown in FIG. 8. The lifting device (not shown) for the service crane 1 may be placed inside the hub 4. After the service crane 1 have been hoisted up to the hub 4, the attachment foundation 8 of the service crane 1 is attached to the wing pitch bearing (not shown) of the hub 4 in the same manner as the wing blade is attached to the wing pitch bearing. This may for instance be performed by fastening devices, such as bolts or the like.

Figure 9:
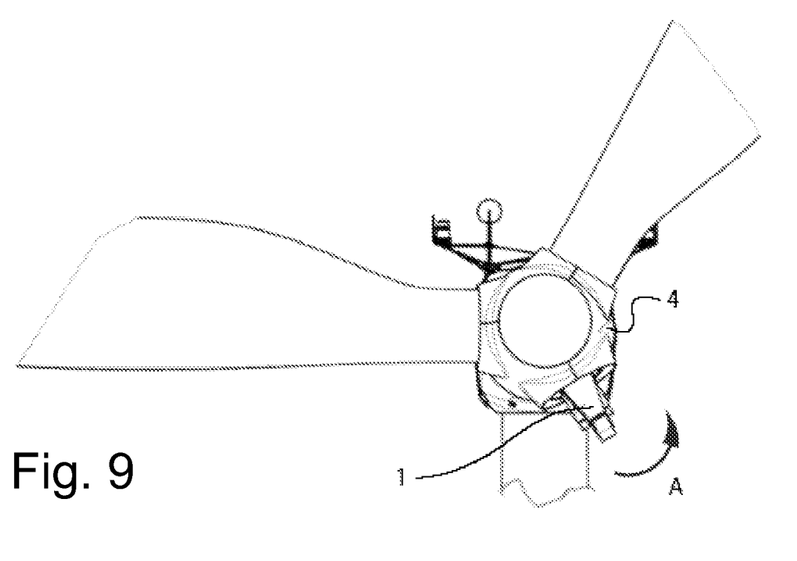
Figure 10:
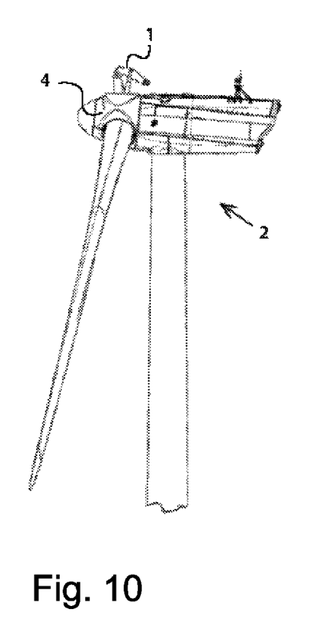
Figure 11:
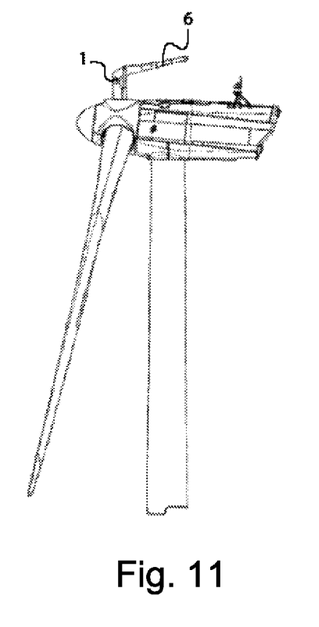
Figure 12:
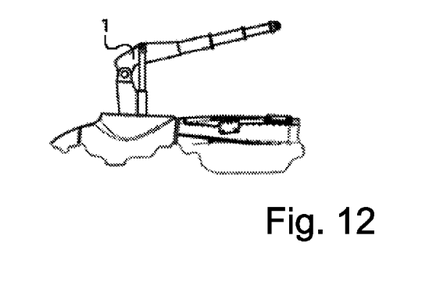

After the service crane 1 has been securely attached to the wing pitch bearing of the hub 4, the entire hub 4 may be turned, as indicated by arrow A in FIG. 9, so that the service crane 1 may be positioned at the top of the hub 4. In FIG. 10, the wind turbine 2 is shown from the side. The service crane 1 has been turned to the top of the hub 4 and is in an unfolded state, so that it will not occupy much room during the mounting of the crane and the subsequent turning of the hub. In FIG. 11, the telescopic arm 6 of the service crane 1 is unfolded, and the service crane is ready for use. An enlarged view of the service crane 1 of FIG. 11 is shown in FIG. 12.

Furthermore, the wing pitch bearing and/or the hub 4 may comprise locking means (not shown), so that the service crane may be fixated and held in place during its operation, whereby unintended movements of the service crane are avoided.

Figure 13:
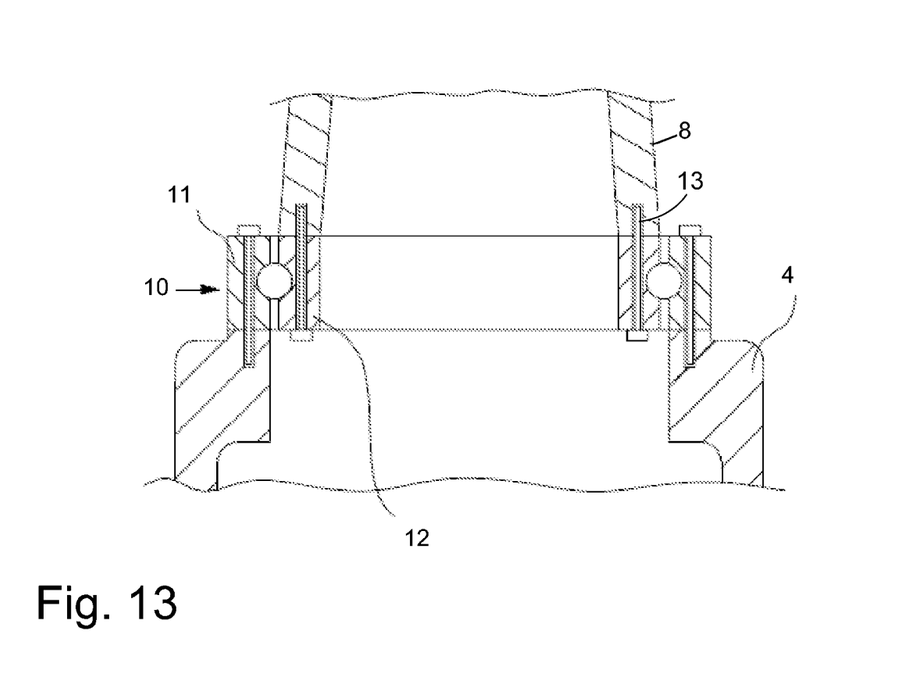
FIG. 13 shows a wing pitch bearing according to the invention in a cross-sectional view.

In FIG. 13 a wing pitch bearing 10 is shown in a cross-sectional view. In this embodiment of the wing pitch bearing 10, it comprises a fixed part 11 and a turnable part 12. The turnable part 12 is arranged on an inside of the fixed part 11; the attachment foundation 8 of the service crane 1 is connected to the turnable part 12. When the attachment foundation 8 is connected with the turnable part 12 of the wing pitch bearing 10, this turnable part 12 may be used to turn the service crane 1. It is furthermore shown how fastening devices 13, for instance bolts, may be used to fasten the attachment foundation 8 to the wing pitch bearing 10. Additionally, the fixed part 11 of the wing pitch bearing 10 is connected to the hub 4.

In another not shown embodiment the attachment foundation may be connected with the fixed part of the wing pitch bearing 10. In this case the service crane preferably comprises a turning device, so that it may be operated, i.e. turned, by this turning device.

In another (not shown) method according to the invention, wherein the wing blade 5 is not removed from the hub, the mounting of a service crane 1 on a wind turbine 2 may comprise the steps of:
- removing one or more fastening devices from a wing pitch bearing of a hub 4, the fastening devices being adapted to hold a wing blade 5 in place on the wing pitch bearing,
- arranging an attachment foundation around the wing blade 5, and
- mounting the attachment foundation on the wing pitch bearing by means of fastening devices.

Although the invention has been described in the above in connection with preferred embodiments of the invention, it will be evident for a person skilled in the art that several modifications are conceivable without departing from the invention as defined by the following claims.

The invention claimed is:

1. A service crane for a wind turbine comprising a nacelle, and a hub, onto which one or more wing blades is attached via a wing pitch bearing, the service crane comprising:
   an attachment foundation for connection to the hub, wherein the service crane is adapted to be mounted on the wind turbine during operation and to be dismounted when not being used,
   wherein the attachment foundation has a configuration that substantially corresponds to the configuration of the wing pitch bearing such that the attachment foundation is mountable on the hub of the wind turbine via the wing pitch bearing, and
   wherein the attachment foundation is connectable with the wing pitch bearing in the same manner as the wing blade is connectable with the wing pitch bearing such that the wing blade must be dismounted from the wing pitch bearing before the attachment foundation of the service crane is mounted to the wing pitch bearing.

2. The service crane according to claim 1, wherein the attachment foundation is mainly connected to the wing pitch bearing from an outside of the hub.

3. The service crane according to claim 1, wherein the wing blade is attached to a tower of the wind turbine when dismounted.

4. The service crane according to claim 1, wherein the attachment foundation has a U-shaped, a horse shoe-shaped, or an at least partly circular configuration.

5. The service crane according to claim 1, where the wing pitch bearing comprises a fixed part and a turnable part, the turnable part being arranged either on an inside of the fixed part or on an outside of the fixed part, wherein the attachment foundation is connected with the fixed part and/or the turnable part.

6. The service crane according to claim 5, wherein the turnable part of the wing pitch bearing is adapted to turn the service crane during operation.

7. A wind turbine comprising the service crane according to claim 1.

8. A method for mounting a service crane on a wind turbine comprising:
   dismounting a wing blade from an attachment interface of a wing pitch bearing of a hub, and
   mounting an attachment foundation of the service crane on the attachment interface of the wing pitch bearing.

9. The method according to claim 8, wherein the wing blade after being dismounted is lowered onto the ground or is attached to a tower of the wind turbine.

10. The method according to claim 9, wherein a nacelle of the wind turbine is yawed away from the wing blade, which has been attached to the tower, before the attachment foundation is connected to the wing pitch bearing.

11. The method according to claim 8, wherein mounting the attachment foundation further comprises mounting the attachment foundation to a turnable part of the wing pitch bearing.

* * * * *